United States Patent [19]

Yoon

[11] Patent Number: 5,320,610
[45] Date of Patent: Jun. 14, 1994

[54] AUTOMATIC RETRACTABLE TROCAR WITH SAFETY SHIELD AND METHOD OF USE

[76] Inventor: InBae Yoon, 2101 Highland Ridge Dr., Phoenix, Md. 21131

[21] Appl. No.: 868,566

[22] Filed: Apr. 15, 1992

Related U.S. Application Data

[63] Continuation-in-part of Ser. No. 808,325, Dec. 16, 1991.

[51] Int. Cl.⁵ .............................................. A61M 5/178
[52] U.S. Cl. .............................................. 604/158
[58] Field of Search ............... 604/164, 167, 93, 110, 604/198, 158, 264; 128/898

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,906,236 | 3/1990 | Alberts et al. . |
| 4,931,042 | 6/1990 | Holmes et al. ............ 604/164 |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Inquiz . |
| 5,030,206 | 7/1991 | Lander ............ 606/185 X |
| 5,053,016 | 10/1991 | Lander . |
| 5,061,251 | 10/1991 | Juhasz . |
| 5,066,288 | 11/1991 | Deniega et al. ............ 604/274 |
| 5,104,382 | 4/1992 | Brinkerhoff et al. ............ 604/165 |
| 5,104,383 | 4/1992 | Shichman ............ 604/167 |
| 5,114,407 | 5/1992 | Burbank ............ 604/164 |
| 5,116,353 | 5/1992 | Green ............ 606/184 |
| 5,127,909 | 6/1992 | Shichman ............ 604/165 |
| 5,152,754 | 10/1992 | Plyley et al. . |
| 5,158,552 | 10/1992 | Borgia et al. . |
| 5,207,647 | 5/1993 | Phelps ............ 604/158 |

FOREIGN PATENT DOCUMENTS

| | | |
|---|---|---|
| 2544262 | 4/1977 | Fed. Rep. of Germany . |
| 1435246 | 11/1988 | U.S.S.R. . |

Primary Examiner—Gene Mancene
Assistant Examiner—Jeffrey A. Smith

[57] ABSTRACT

An automatic retractable safety trocar instrument includes a portal sleeve, a trocar disposed within the portal sleeve and a safety shield disposed between the portal sleeve and the trocar. The trocar is movable automatically from an operative position wherein a sharp distal end of the trocar protrudes from the portal sleeve to a retracted position wherein the sharp distal end is protected within the instrument upon penetration into a cavity in the body. The safety shield is automatically movable proximally from an extended position during penetration of tissue and distally toward the extended position upon introduction of a distal end of the portal sleeve in an anatomical cavity such that a distal end of the safety shield contacts tissue within the cavity and moves the tissue away from the cavity wall. A method of creating a space between a wall of an anatomical cavity and a layer of tissue within the cavity includes penetrating the cavity wall with the sharp tip of a penetrating member disposed within a portal sleeve to position a distal end of the portal sleeve within the cavity and extending a safety shield to protrude beyond the sharp tip and the cavity wall whereby a blunt distal end of the safety shield moves the tissue away from the wall maintaining a space between the tissue and the wall.

60 Claims, 2 Drawing Sheets

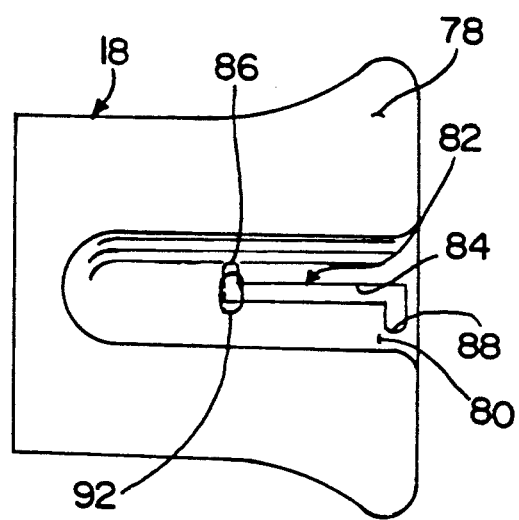

AUTOMATIC RETRACTABLE TROCAR WITH SAFETY SHIELD AND METHOD OF USE

CROSS REFERENCE TO RELATED APPLICATIONS

This application is a continuation in-part of pending patent application Ser. No. 07/808,325 (pending), filed Dec. 16, 1991. The specifications of pending patent applications Ser. No. 07/800,507 (pending), filed Nov. 27, 1991, Ser. No. 07/805,506 (pending), and Ser. No. 07/808,325, filed Dec. 16, 1991, Ser. No. 07/817,113 (pending), filed Jan. 6, 1992 and Ser. No. 07/848,838 (pending), filed Mar. 10, 1992, all naming InBae Yoon as inventor are incorporated herein by reference.

BACKGROUND OF THE INVENTION

1. Field of the Invention

The present invention pertains to safety penetrating instruments and, more particularly, to safety penetrating instruments having portal sleeves, penetrating members disposed within the portal sleeves and having sharp tips for penetrating cavity walls and safety shields disposed between the portal sleeves and the penetrating members with automatic retraction of the penetrating members within the penetrating instrument upon penetration to protect tissue and organ structures within the cavities from the sharp tips of the penetrating members.

2. Discussion of the Prior Art

Penetrating instruments are widely used in medical procedures to gain access to anatomical cavities of various sizes; and, in particular, use of penetrating instruments has become an extremely popular and important first step in endoscopic, or least invasive, procedures to establish an endoscopic portal for many various procedures, with access being established via a portal sleeve positioned during penetration into the cavity with the penetrating instrument. Such penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety trocars having a spring-biased protective shield disposed between an outer sleeve and an inner trocar are marketed by Ethicon, Inc. as the Endopath and by United States Surgical Corp. as the Surgiport. U.S. Pat. No. 4,535,773 to Yoon, No. U.S. Pat. No. 4,601,710 to Moll and U.S. Pat. No. 4,654,030 to Moll et al are illustrative of such safety trocars. A trocar disposed within a portal sleeve and retractable within the sleeve in response to an electrical signal generated when force from tissue contact is removed from the sharp tip of the trocar is set forth in U.S. Pat. No. 4,535,773 to Yoon.

One of the limitations of many prior art safety penetrating instruments is that the trocars cannot be optionally removed from the safety shields upon penetration into body cavities to allow lumens of the safety shields communicating with the body cavities to be used to perform various medical procedures, such as evacuating and supplying fluids to the body cavities, via the lumens. Many prior art safety penetrating instruments have other limitations in that the safety shields are not retractable within the portal sleeves upon penetration into body cavities, and visual, tactile and aural confirmation of cavity penetration are not effectively provided. A disadvantage of prior art methods of penetrating body cavities with safety penetrating instruments is that extension of the safety shields beyond the portal sleeves is not used to create spaces or increase the size of spaces within the body cavities upon penetration of walls of the body cavities such as is useful in forming or enlarging a space between membranes, in penetrating plueral cavities to create or increase the size of a space between the perietal and visceral walls, the epidural canal, thoracostomy and where the cavities being penetrated are very narrow.

SUMMARY OF THE INVENTION

Accordingly, it is a primary object of the present invention to overcome the above-mentioned disadvantages of prior art safety penetrating instruments.

Another object of the present invention is to provide a safety penetrating instrument for creating a space or increasing the size of a space between a wall of a body cavity and a layer of tissue within the body cavity upon penetration of the cavity wall with the safety penetrating instrument.

A further object of the present invention is to provide a method for maintaining a space between a wall of a body cavity and a layer of tissue within the body cavity upon penetration of the cavity wall with a safety penetrating instrument including moving the tissue away from the cavity wall with extension of a safety shield of the safety penetrating instrument.

It is also an object of the present invention to provide an automatic retractable safety trocar instrument having a portal sleeve, a trocar disposed within the portal sleeve and a safety shield disposed between the trocar and the portal sleeve with the safety shield being extended from the portal sleeve upon penetration of a body cavity wall with the trocar to move tissue within the body cavity away from the wall creating or increasing the size of a space between the tissue and the wall.

A further object of the present invention is to provide an automatic retractable safety trocar instrument having a portal sleeve, a trocar disposed within the portal sleeve and a safety shield disposed between the trocar and the portal sleeve and movable to an extended position upon penetration of a cavity wall such that a distal end of the safety shield protrudes beyond the cavity wall a distance corresponding to the size of a space to be created with the safety shield adjacent the cavity wall.

An additional object of the present invention is to provide an automatic retractable safety trocar instrument having a portal sleeve, a trocar disposed within the portal sleeve and a safety shield disposed between the trocar and the portal sleeve and automatically movable to an extended position wherein a distal end of the safety shield protrudes beyond a distal end of the portal sleeve a distance corresponding to the size of a potential space to be created with the safety shield between a wall of a body cavity and a layer of tissue within the body cavity upon introduction of the portal sleeve into the body cavity.

The present invention has an additional object of allowing a trocar to be removed from a safety shield disposed around the trocar and within a portal sleeve upon introduction of the portal sleeve into a body cavity such that a lumen of the safety shield communicating with the body cavity can be used to perform various medical procedures.

Yet another object of the present invention is to automatically retract a trocar of an automatic retractable safety trocar instrument to a safe, protected position within the instrument in response to distal movement of an operating member upon penetration into an anatomical cavity with a safety shield disposed around the trocar being moved to an extended position from a portal sleeve receiving the safety shield.

A still further object of the present invention is to automatically retract a safety shield and a trocar of an automatic retractable safety trocar instrument to a safe, protected position within a portal sleeve in response to distal movement of an operating member upon penetration into an anatomical cavity.

The present invention has as a further object to provide an automatic retractable safety trocar instrument in a rest position with a sharp distal tip of a trocar in a retracted position within the instrument and a safety shield disposed around the trocar in an extended position protruding from a portal sleeve receiving the safety shield while a hub coupled with the trocar and the safety shield is engaged with a housing coupled with the portal sleeve and to allow the trocar to be manually moved to an operative extended position with the sharp distal tip extending beyond a distal end of the portal sleeve.

A further object of the present invention is to provide an automatic retractable safety trocar instrument in a rest state with bias devices therein disposed in relaxed or unloaded states and moved to bias or loaded states prior to penetration of tissue.

The present invention has an additional object of allowing safe introduction of portal sleeves into body cavities of very small size, such as spinal canal, epidural canal, synovial, pleural or pericardial cavities, for example, by automatically retracting a sharp tip of a trocar within a portal sleeve after the cavities are penetrated thereby and allowing spaces within the cavities to be created or increased in size with extension of a safety shield within the cavities beyond a distal end of the portal sleeve.

Some of the advantages of the present invention over the prior art are that small or narrow anatomical cavities can be safety penetrated, spaces can be created or enlarged within body cavities in a safe manner, the lumen of the safety shield can be utilized to conduct various medical procedures, such as irrigation and aspiration, the safety shield can be extended from the portal sleeve a controlled distance to maintain a space within a body cavity corresponding to the distance to facilitate various medical procedures, the automatic retractable safety trocar instrument can be provided and stored in a rest state with the sharp distal tip of the trocar withdrawn into the portal sleeve in a safe, protected position, the safety shield extended from the portal sleeve and the bias devices in relaxed states, portal sleeves can safely be introduced into anatomical cavities of various sizes to expand the use of least invasive procedures in many areas including, for example, the cardiac, brain, vascular, chest, genitourinary system, breast and spinal fields, both the safety shield and the trocar can be automatically retracted within the portal sleeve upon penetration into and formation of a space within a body cavity as is useful to separate membranes as well as in various other medical procedures, the automatic retractable safety trocar instrument encourages the use of a smooth, continuous penetrating motion by the surgeon thereby reducing trauma, tears and irregular surfaces in the tissue of the cavity wall, with the use of a threaded distal tip on the trocar, penetration of the narrowest of anatomical cavities can be achieved in a safe manner in view of the gradual advancement of the trocar coupled with immediate automatic retraction of the trocar upon entry into the cavity, with the trocar in a retracted position and the safety shield in an extended position from the portal sleeve upon penetration of tissue, redundant protection is provided for tissue and organ structures within anatomical cavities, safe penetration of anatomical cavities is achieved while permitting injection or evacuation of fluids, a single puncture can be used for both insufflation and forming an endoscopic portal thereby simplifying diagnostic and surgical procedures, the sharp tip of the trocar is in a protected, safe position prior to penetration of tissue ensuring safety of medical personnel during use, trauma and damage to tissue is minimized, tissue jamming and trapping is avoided and automatic retractable safety trocar instruments according to the present invention can be inexpensively manufactured to be reusable or disposable for universal use.

The present invention is generally characterized in an automatic retractable safety trocar instrument including a portal sleeve, a trocar disposed within the portal sleeve and having a sharp distal tip for penetrating tissue and a safety shield disposed between the portal sleeve and the trocar and biased to an extended position protruding distally from the portal sleeve. The safety shield is movable proximally against the distal bias during penetration of tissue of the cavity wall to expose the sharp tip of the trocar and is movable distally thereafter toward an extended position within the cavity, with the sharp tip of the trocar automatically moving proximally to a safe, retracted position in response to distal movement of an operating member. With the safety shield extended within the cavity, a distal end of the safety shield contacts tissue within the cavity and pushes the tissue away from the cavity wall thusly creating or increasing the size of a space between the tissue and the cavity wall. The distance that the safety shield extends into the cavity can be controlled to correspond to a desired size of a potential space to be created within the anatomical cavity upon introduction of the portal sleeve distal end therein. Extension of the safety shield is caused by a bias device that is in a relaxed or unloaded state in the extended position for the safety shield. Retraction of the trocar is caused by a bias device that is in a relaxed or unloaded state when the trocar is in a retracted position. The trocar can be locked in the retracted position and; accordingly, the automatic retractable safety trocar instrument can be supplied with the trocar in the retracted position and the safety shield in the extended position and the bias devices in relaxed or unloaded states. The trocar can be manually moved from the retracted position to an operative position with the sharp tip of the trocar protruding beyond the distal end of the portal sleeve to be locked in the operative position by a latch that is released by distal movement of the operating member upon penetration into the cavity. Alternatively, the trocar can be locked against retraction in the operative position for use as a standard safety trocar penetrating instrument. The trocar alone can retract or both the trocar and the safety shield can retract upon introduction of the distal end of the portal sleeve into an anatomical cavity, and the distance that the safety shield extends into the anatomical cavity beyond the distal end of the portal sleeve prior to retraction can be controlled. The trocar can be removed from the safety shield allowing the safety shield to remain in place in an extended position within an anatomical cavity such that the lumen of the safety shield can be utilized to perform various medical procedures. Alternatively, both the safety shield and trocar can be removed from the portal sleeve leaving the portal sleeve in place with the anatomical cavity by a method of creating a space between a wall of an anatomical cavity and the layer of tissue within the cavity according to the present invention includes the steps of penetrating the cavity wall with the sharp tip of a penetrating member disposed within a portal sleeve to position a distal end of the portal sleeve within the cavity and extending a safety shield to protrude beyond the sharp tip of the penetrating member and the cavity wall whereby a blunt distal end of the portal sleeve moves the tissue away from the wall maintaining a space between the tissue and the wall.

These and other objects and advantages of the present invention will become apparent from the following description of the preferred embodiments taken in conjunction with the accompanying drawings.

BRIEF DESCRIPTION OF THE DRAWINGS

FIG. 2 is a side view of the hub of the automatic retractable safety trocar instrument of FIG. 1.

DESCRIPTION OF THE PREFERRED EMBODIMENTS

Figure 1:
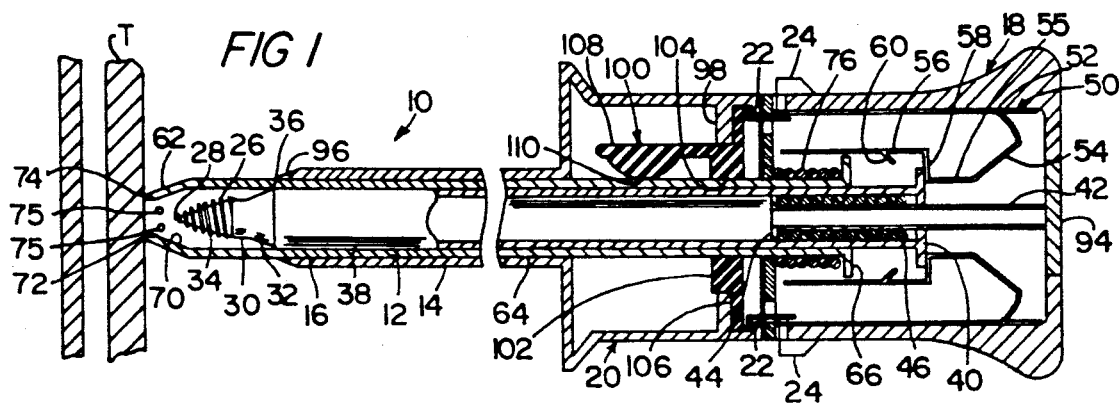
FIG. 1 is a broken side view, partly in section, of an automatic retractable safety trocar with safety shield instrument according to the present invention prior to penetrating a wall, such as a perietal wall, of an anatomical cavity.

An automatic retractable safety trocar instrument 10 according to the present invention is illustrated in FIG. 1 and includes an elongate penetrating member such trocar 12, a portal sleeve 14 concentrically disposed around trocar 12, a safety shield 16 concentrically disposed between trocar 12 and portal sleeve 14, a hub 18 mounting trocar 12 and safety shield 16 and a valve housing 20 mounting portal sleeve 14. The hub 18 can be latched to housing 20 with the use of any suitable releasable mechanism, such as detents 22 operated by buttons 24, allowing the hub to be removed from the housing withdrawing the trocar and safety shield from the portal sleeve. Accordingly, the automatic retractable safety trocar instrument 10 can be considered to be formed of a portal unit and a penetrating unit, the portal unit including portal sleeve 14 and housing 20 and the penetrating unit including trocar 12, safety shield 16 and hub 18.

Trocar 12 is preferably made of a medical grade material, such as stainless steel, and has an outer diameter or size dependent upon the surgical procedure to be performed and the anatomical cavity to be penetrated. The trocar 12 has a distal end 26 terminating at a sharp tip 28 for penetrating anatomical tissue. The distal end 26 can have various configurations including the various distal end configurations shown in applicant's co-pending patent application Ser. No. 07/817,113, filed Jan. 6, 1992, the specification of which is incorporated herein by reference. As shown in FIG. 1, the distal end has a conical shape terminating distally at sharp tip 28 and proximally at a peripheral junction at cylindrical neck 30 which, in turn, terminates proximally at a frusto-conical shoulder 32. A helical thread 34 extends along the conical distal end from the peripheral junction at neck 30 to the tip 28. Shoulder 32 terminates proximally at a diametrically larger peripheral junction 36 joining the shoulder to an elongated body 38 which can be cylindrical or have any desirable configuration in cross-section. Body 38 extends proximally from the distal end junction 36 to terminate at a retraction plate 40 at a proximal end of the trocar, the proximal end being disposed in hub 18 with body 38 passing through an aperture in a front wall of the hub. The body 38 can be hollow or tubular along the length of the trocar, and an aperture (not shown) can be disposed at the distal end 26 to allow communication entirely through the instrument 10 where a valve is carried on a rear wall of hub 18 as set forth in applicant's co-pending patent application Ser. No. 07/808,325, filed Dec. 16, 1991, the specification of which is incorporated herein by reference, or the body can be partly hollow or tubular to receive a tube 42 extending distally from the rear wall of the hub and into the hollow proximal end of the trocar. A retracting mechanism engages the proximal end of the trocar 12 and includes the retraction plate 40, an annular rim 44 formed on tube 42 to be disposed within the proximal end of the trocar with tube 42 extending through an opening in plate 40 and a coiled helical retracting spring 46 disposed around tube 42 and mounted in compression between rim 44 and plate 40 to bias the trocar 12 in a proximal direction. To simplify assembly of the automatic retractable safety trocar instrument 10, plate 40 can be removably attached to the cylindrical body 38 such as by threads and the like. The distal end of the trocar 12 can be removably mounted on the cylindrical body 38 allowing various distal tips to be interchangeably mounted on the cylindrical body of the trocar.

A locking and releasing or trigger mechanism 50 is disposed in hub 18 to actuate the retracting mechanism and includes a latch or locking spring having a substantially flat base 52 secured to a wall of hub 18 with an arm 54 bent inwardly therefrom and extending angularly distally in the direction of a longitudinal axis of the automatic retractable safety trocar instrument 10. Arm 54 includes a section 55 extending parallel with the longitudinal axis, and a bent locking finger or member 56 is joined to a distal end of section 55 by a shoulder 58, the shoulder 58 engaging the retraction plate 40 to prevent movement of the retracting mechanism and, therefore, the trocar, in a proximal direction when the locking spring is in its normal position as illustrated in FIG. 1. The finger 56 extends distally of shoulder 58, and the trigger mechanism 50 has a releasing or trigger member 60 disposed along finger 56 distally or forwardly of the shoulder 58. The trigger member 60 extends rearwardly or proximally from finger 56 at an angle to allow movement of an operating member or flange thereby in a proximal direction without causing bending of arm 54 as will be explained further below. The shoulder 58 acts as a positive stop or abutment member to limit proximal movement of the operating flange by abutment with plate 40, and trigger 60 is positioned distally of shoulder 58 by a distance corresponding to the distal movement desired of the flange or operating member prior to automatic retraction, as will be explained in more detail hereinafter. The locking and releasing or trigger mechanism can be mounted at any suitable location on the hub and provided with any required configuration to act as a stop or abutment to prevent proximal movement of the trocar and to be actuated or released by a distally moving operating member including the configurations and arrangements set forth in applicant's co-pending patent applications Ser. Nos. 07/808,325, 07/800,507, 07/805,506, 07/808,325 and 07/848,838 referenced above and the specifications of which are incorporated herein by reference. The locking and releasing mechanism can be made as one piece or multiple pieces dependent upon the hub construction and the operating member utilized to actuate the trigger. As shown, locking member 56 and trigger 60 are unitarily, integrally formed of a single strip of resilient, spring material such as metal or plastic. The locking and releasing or trigger mechanism can include one or more locking springs; and, as shown in FIG. 1, a pair of locking springs are disposed in hub 18 at diametrically opposed locations along plate 40.

Figure 3:
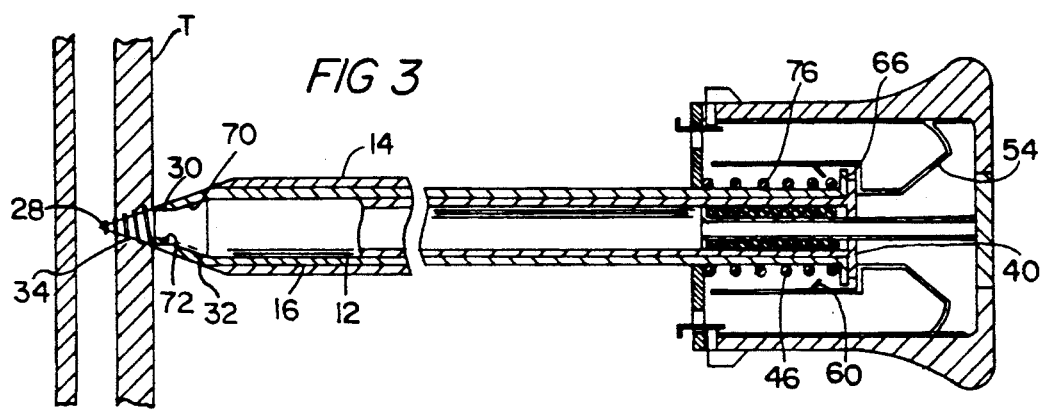
FIG. 3 is a broken side view, partly in section, of the automatic retractable safety trocar instrument of FIG. 1 during penetration of the perietal wall.

Safety shield 16 is preferably made from a cylindrical length of a rigid or flexible medical grade material, such as stainless steel or plastic, dependent upon use of the automatic retractable safety trocar instrument, and has a blunt distal end 62 with a configuration to extend beyond and protect sharp tip 28 of trocar 12 in an extended position. The safety shield has a cylindrical tubular body 64 extending along the cylindrical body 38 of the trocar 12 and through the opening in the front wall of hub 18. Tubular body 64 terminates at an operating member or flange 66 at a proximal end of the safety shield, the operating flange 66 being disposed distally of the retraction plate 40. The distal end of the safety shield 16 is configured to mate with the distal end of the trocar 12 in a retracted position for the safety shield and includes a tapering conical wall distally joined to tubular body 64 and having an angular inner surface segment 70 distally joined to an inner surface of the tubular body 64 and a cylindrical inner surface segment 72 extending distally from the angular inner surface segment to a blunt distal peripheral edge 74. The angular inner surface segment 70 is disposed at the same angle relative to a longitudinal axis of the trocar as the angle of shoulder 32 relative to the trocar longitudinal axis, and the cylindrical inner surface segment 72 has an axial length substantially equal to the axial length of trocar neck 30. The peripheral distal edge 74 of the safety shield is shown as being circular, which is preferred if the trocar tip is conical rather than faceted; however, distal edge 74 can be scalloped or formed of curved segments, as well as various other configurations including the configurations shown in applicant's copending patent application Ser. No. 07/817,113, filed Jan. 6, 1992, the specification of which is incorporated herein by reference. One or more apertures 75 can be provided in the safety shield distal end providing fluid communication with an anatomical cavity through the lumen of the safety shield when the trocar is withdrawn from hub 18. As shown in FIG. 3, when the safety shield is in a retracted position, the angular inner surface segment 70 is in contact with shoulder 32 along the length thereof while cylindrical inner surface segment 72 is in contact with neck 30. Accordingly, the distal end of the automatic retractable safety trocar instrument has a smooth profile presenting minimal resistance to tissue as a cavity wall is penetrated. A coiled helical operating spring 76 is disposed concentrically around the tubular body 64 of the safety shield and is connected between operating flange 66 and the front wall of hub 18, the operating spring 76 being mounted in tension to bias the safety shield in a distal direction to an extended position as shown in FIG. 1 with the distal end of the safety shield protruding beyond the portal sleeve 14.

Hub 18 can be made of any suitable material to be disposable or reusable and has an external configuration to cooperate with housing 20 to be easily grasped with one hand for use in penetrating tissue. Hub 18 can have any desired configuration in cross-section and is shown in FIG. 1 as being substantially rectangular while having a flared profile adjacent the rear wall thereof. As shown in FIG. 2, a side wall 78 of the hub has a central recessed channel 80 aligned with a longitudinal axis of the automatic retractable safety trocar instrument, and a slot 82 is disposed in the channel 80 and is formed of a longitudinal portion 84 aligned with the longitudinal axis of the instrument 10, a distal transverse portion 86 and a proximal transverse portion 88. A pin (not shown) is threadedly secured along the periphery of plate 40 and extends through slot 82, the pin having a "T" configuration to terminate at an external knob 92. As previously noted, a valve of any conventional design can be provided in the rear wall of the hub in alignment with the lumen of tube 42 to allow passage of fluid entirely through the instrument for additional confirmation of cavity penetration via leakage detection and for irrigation and aspiration when the trocar is hollow along its length or provided with an aperture at the distal end to establish fluid communication through the instrument. A plug or insert 94 is removably mounted by any suitable means, such as by threads or the like, in the rear wall of the hub 18 such that the tube 42 and, therefore, the trocar 12, can be withdrawn from the hub 18. Where the plate 40 is formed separately from the body 38, the plate can be removed from the trocar allowing the tube 42 to be withdrawn therefrom such that the insert 94 and the tube can be replaced in hub 18. The tube 42 can be removably coupled with the insert 94 allowing the insert alone to be replaced within the rear wall of the hub. Where a valve is provided in the rear wall of the hub 18, the valve can be provided in the insert 94 in communication with the lumen of the safety shield permitting various medical procedures to be conducted through the lumen with the trocar withdrawn from the hub and the safety shield remaining within the anatomical cavity.

Portal sleeve 14 is preferably made of a substantially cylindrical length of rigid or flexible material, such as stainless steel or other suitable, medically acceptable, plastic or metal material, and can be transparent or opaque. The portal sleeve has a distal end 96 having a configuration to produce a smooth profile with the safety shield 16 when the instrument 10 is in an operating state to penetrate tissue, as shown in FIG. 3, and the portal sleeve has a proximal end mounted in or formed with a front wall of valve housing 20 with a lumen extending between the distal and proximal ends. Housing 20 can be made of any suitable material to be disposable or reusable and has a configuration in cross section corresponding to the cross-sectional configuration of hub 18 with a flared external profile adjacent the front wall of the housing facilitating grasping during use. A wall 98 extends inwardly from housing 20 at a rear end thereof at a position distally spaced from the rear end of the housing to produce a recess for receiving detents 22, the wall 98 having a central passage for receiving a valve assembly 100. Valve assembly 100 can have any conventional configuration to produce a closed or sealed condition upon removal of the penetrating unit from the portal unit. As shown in FIG. 1, valve assembly 100 is formed of a unitary, one-piece integral construction of rubber or soft plastic to facilitate sealing to prevent fluid flow through the instrument when the penetrating unit is removed. The valve assembly 100 is formed of a body 102 having a passage 104 therethrough and a proximal flange 106 extending outwardly therefrom to be received in the recess at the rear end of the housing 20. The body 102 has a peripheral configuration to fit snugly within the passage through wall 98, and a valve member 108 extends distally from body 102 and has a normally sealed position with a hemispherical bulging end 110 received in the valve seat formed at the end of passage 104 to produce a normally closed, sealed configuration. To provide assisted bias toward the sealed configuration, a spring member can be embedded within the valve assembly 100 to bias the valve member 108 toward the valve seat. While the face of the valve seat is illustrated as being transverse to the longitudinal axis of the automatic retractable safety trocar instrument 10, the valve seat can be angularly oriented as set forth in applicant's co-pending patent application Ser. No. 07/848,838, filed Mar. 10, 1992, the specification of which is incorporated herein by reference.

Figure 4:
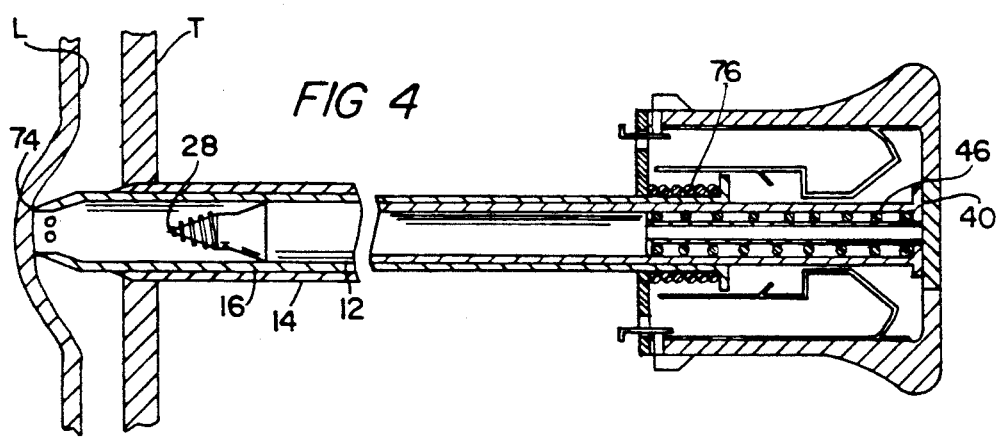
FIG. 4 is a broken side view, partly in section, of the automatic retractable safety trocar instrument of FIG. 1 following penetration of the perietal wall with the safety shield in an extended position to move a layer of tissue, such as a visceral wall, away from the parietal wall to increase the size of the space between the perietal and visceral walls.

In use, the automatic retractable safety trocar instrument 10 is normally provided in a rest state wherein the distal end 26 of trocar 12 is retracted within portal sleeve 14 to be in a safe protected condition, the rest state coinciding with the retracted position for the trocar shown in FIG. 4. In the rest state, retracting spring 46 is in a relaxed, unbiased or unloaded state, with plate 40 abutting the insert 94 or rear wall of the hub 18 carrying with it trocar 12. Operating spring 76 is similarly in an unbiased state in the rest position. Accordingly, with the automatic retractable safety trocar instrument initially provided in a rest state, no loading of the springs 46 and 76 exist such that the strength of the springs is not weakened and shelf life is increased. With the automatic retractable safety trocar instrument in the rest state, knob 92 will be disposed at a proximal end of the longitudinal slot portion 84 and can be rotated to be received in proximal transverse slot portion 88 to be locked in that position to assure that the sharp distal end 28 of the trocar remains in a protected position. By forming plate 40 separate from the trocar and rotatably mounting the plate 40 on the proximal end of the trocar, knob 92 can be rotated in slot 88 without rotation of the trocar. In the rest state, the safety shield 16 will be in an extended position with the distal end 62 of the safety shield protruding beyond the distal end 96 of the portal sleeve. When it is desired to utilize the instrument 10 to penetrate tissue to introduce the portal sleeve into an anatomical cavity, the knob 92 is grasped and moved distally within longitudinal slot portion 84 to the distal end thereof causing retraction plate 40 to move over arm 54 and to be locked in place adjacent the shoulders 58 as shown in FIG. 1. Locking of the retraction plate can be confirmed by feel and sound as the locking member snaps into place and also visually by viewing the position of knob 92 relative to slot 82. Additionally, the tube 42 can be made a first predetermined color and the proximal end of the trocar can be made a second, different predetermined color with a portion of the hub 18 along the slot 82 or overlying the tube 42 being made transparent. Accordingly, the color of the trocar proximal end will be observed along the slot when the trocar is in the retracted position of FIG. 4, and the color of the tube will be seen along the slot when the trocar is in the operative position of FIG. 1 providing further visual confirmation of locking of the retraction plate. With the instrument 10 in the extended or operative condition shown in FIG. 1, the distal end junction 36 of the trocar will be substantially aligned with the distal end 96 of the portal sleeve. The safety shield will remain in an extended position with the peripheral edge 74 of the safety shield protruding beyond the distal end 96 of the portal sleeve a distance corresponding to the size of a potential space to be created within an anatomical cavity upon introduction of the portal sleeve therein, and the safety shield protrudes beyond the sharp tip of the trocar to protect the sharp tip.

The instrument can now be utilized to penetrate tissue and enter an anatomical cavity in two manners. In a first manner, knob 92 is rotated into distal transverse slot portion 86 which allows the instrument to be used as a standard safety trocar with the trocar being prevented from retracting and the safety shield being movable from the extended position to a retracted position wherein the distal edge 74 of the safety shield is substantially aligned with the junction of the trocar at neck 30 via movement of the safety shield against the bias of spring 76 due to a proximal force from tissue contact at the distal end of the safety shield during penetration of tissue. Accordingly, upon penetration of a wall of an anatomical cavity, the distal end of the safety shield will automatically return to the extended position due to the distal bias while the trocar is prevented from retracting. In a second manner, the hub and housing are grasped by the surgeon and the instrument is forced against tissue T, such as tissue forming a wall of a body cavity such as a perietal wall, as shown in FIG. 1, causing safety shield 16 to move proximally against the bias of operating spring 76 until operating flange 66 abuts plate 40 and the distal peripheral edge 74 of the safety shield is substantially aligned with the junction of the trocar at neck 30 as shown in FIG. 3. When the flange or operating member 66 moves proximally, the operating member causes trigger members 60 to deflect proximally such that the flange 66 moves proximally past the trigger members. The trigger members 60 can be positioned at varying distances from the operating flange 66 to control the amount of distal movement of the operating member required before the trocar is retracted. With the safety shield in the retracted position, the angular inner surface segment 70 will be disposed along the conical shoulder 32 of the trocar and the cylindrical inner surface segment 72 will be disposed along the trocar neck 30 to present a substantially smooth profile with the distal end of the trocar and the portal sleeve as shown in FIG. 3. The instrument is forced through the tissue T to enter the anatomical cavity with the sharp distal tip 28 of the trocar extending beyond the distal end of the portal sleeve and the safety shield and, where the helical thread 34 is provided, a slow rotational motion can be used during penetration of the cavity wall to ensure safe introduction of the portal sleeve in even the narrowest of cavities. Once the distal end of the instrument has passed through the tissue T, operating spring 76 will move safety shield 16 distally causing distal movement of operating flange 66 to engage trigger members 60 and flex arms 54 in a direction outwardly from the longitudinal axis of the instrument such that shoulders 58 are moved out of abutment with retraction plate 40. Accordingly, retracting spring 46 will automatically move the retraction plate and the trocar to the retracted position shown in FIG. 4 with the sharp distal tip 28 of the trocar disposed within the portal sleeve in a safe protected position. The operating spring 76 will bias the safety shield 16 to the extended position allowing the blunt distal end 74 of the safety shield to contact a layer of tissue L, such as a visceral wall, within the anatomical cavity thusly creating or enlarging a space between the layer L and the cavity wall. In the extended position, the safety shield will protrude from the distal end of the portal sleeve a distance substantially equal to the distance that the distal end of the safety shield protrudes beyond the cavity wall and this distance corresponds to the size of the gap or space created and maintained between the tissue layer and the cavity wall via extension of the safety shield as shown in FIG. 4. The distal end of the safety shield is disposed further from the cavity wall than the tissue layer when the safety shield is in the extended position within the cavity such that the safety shield causes the tissue to move or bulge in a direction outwardly from the cavity wall to create, enlarge or maintain a space between the tissue and the cavity wall.

Figure 5:
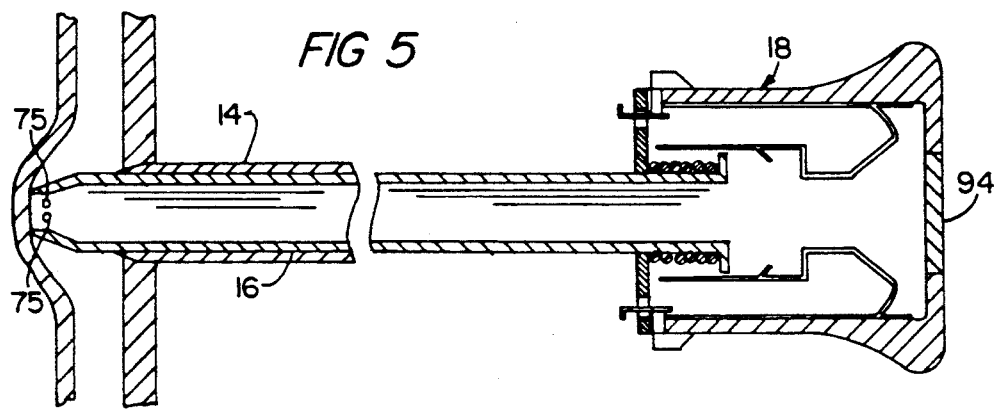
FIG. 5 is a broken side view, partly in section, of the automatic retractable safety trocar instrument of FIG. 1 following penetration of the perietal wall with the trocar having been removed from the hub and the safety shield remaining in place within the anatomical cavity.

Once the distal end of the instrument has entered into the anatomical cavity and the trocar has moved to the retracted position, the portal sleeve will have been introduced into the cavity such that the trocar can be withdrawn from the hub 18 via removal of insert 94 allowing the safety shield to remain in place in the anatomical cavity in an extended position as shown in FIG. 5. The tube 42 can be removed from the insert 94 and the insert replaced on the rear wall of the hub creating a sealed environment therein or the tube 42 can be withdrawn from the trocar permitting the tube and the insert to be replaced in the hub. Where a valve is provided in the insert 94, the lumen of the safety shield communicating with the anatomical cavity can be utilized to aspirate fluid from the cavity or to introduce fluid to the cavity via the apertures 75. A valve can be provided along the insert 94 or at various other locations along the instrument to communicate with the lumen of the safety shield upon withdrawal of the trocar therefrom. Additionally, the penetrating unit can be withdrawn from the portal unit leaving the portal sleeve in place within the cavity and; when the penetrating unit is withdrawn, the valve member 108 will engage the valve seat or passage 104 to seal the portal unit from fluid flow therethrough from insufflation pressure. The one-piece construction of valve assembly 100 has the advantages of being inexpensive to manufacture by molding and as being easily replaceable when used with reusable portal units. Additionally, the axial length of passage 104 produces an elongate seal with the safety shield 16 minimizing escape of fluid during cavity penetration; and, if an instrument of a different size than the safety shield is to be introduced after withdrawal of the penetrating unit, the valve assembly can be easily interchanged to install a valve assembly having a passage 104 of a diameter to seal along the different sized instrument. Confirmation of penetration into the anatomical cavity can be sensed or detected visually from movement of knob 92 along the slot 82 in that the knob will move to the proximal end of the slot with retraction of the trocar, tactilely from feel from the surgeon's hand when the trocar suddenly retracts, and aurally from the sound of the trocar retracting upon penetration. Where the tube and the proximal end of the trocar are different colors and a portion of the hub is transparent, confirmation of penetration can be detected visually via an observable color change as the proximal end of the trocar covers the tube.

Various other structural configurations and arrangements for the retracting spring, the retraction mechanism, the operating spring, the operating member, the locking and releasing or trigger mechanism, the trocar, the safety shield, the valve assembly, the hub and the housing can be employed in addition to those shown herein by way of example, including the various other configurations and arrangements disclosed in applicant's copending patent applications Ser. Nos. 07/808,325, 07/800,507, 07/805,506, 07/808,325, 07/817,113, 07/848,838, the specifications of which are incorporated herein by reference. The automatic retractable safety trocar instrument 10 can be modified such that both the trocar and the safety shield retract within the portal sleeve upon penetration of a cavity wall, and applicant's copending patent application Ser. No. 07/808,325, filed Dec. 16, 1991, and incorporated hereby by reference, illustrates various configurations and arrangements of safety shields retractable with a trocar within a portal sleeve upon penetration of cavity walls.

Automatic retractable safety trocar instruments according to the present invention can incorporate the various features and modifications disclosed herein and in applicant's above referenced copending patent applications incorporated herein by reference. For example, the trocar can have distal ends of various configurations, such as pyramidal, conical, threaded and multifaceted, the positions of the retracting and operating springs can be coaxial, concentric, laterally offset, within the trocar or external of the trocar. Where the springs are laterally offset, the hub can have a reduced length; and, where the springs are aligned with the longitudinal axis of the instrument, the hub can have a reduced width. When the springs are concentrically disposed and positioned within the trocar, the overall size of the hub can be minimized. The springs can be loaded or biased in either tension or compression; and, preferably, the instruments are provided for use with both the retracting spring and the operating spring in a relaxed or unloaded state to increase shelf life. The pin and slot arrangement between the trocar and the hub provides the surgeon with control over the instrument to allow use without retraction and to allow manual movement of the trocar to an operative position with the distal end of the trocar extending from the distal end of the portal sleeve and in alignment therewith to have the function and appearance of a standard safety trocar penetrating instrument. By disposing the knob 92 in a recessed channel, accidental dislodging of the pin in the slot 82 is prevented. Movement of the pin also produces a visual indication of retracting and extending operation of the instrument which can also be determined by feel and sound both upon movement of the trocar to the extended position and to the retracted position as well as visually by a color change seen along the slot via a transparent or visible portion of the hub where the tube and the proximal end of the trocar are of different colors.

The hub arrangement used in the automatic retractable safety trocar instruments will depend upon procedural requirements and the springs and locking and releasing mechanisms housed therein. A valve can be provided along the rear wall of the hub and, in particular, in the insert 94, allowing fluid communication through the trocar where the trocar is hollow or through the safety shield where the trocar is withdrawn from the hub.

The locking and releasing mechanism chosen for the automatic retractable safety trocar instruments will depend upon ease of manufacture and assembly, holding or locking forces required and releasing forces required. The spacing of the trigger from the operating member during tissue penetration will determine the distal movement required of the operating member prior to automatic retraction of the trocar. Accordingly, the distance that the safety shield is allowed to protrude beyond the portal sleeve prior to retraction of the trocar, and of the safety shield where the safety shield also retracts, can be controlled such that the safety shield can push tissue away from the cavity wall prior to retraction, and the distance can be less than full extension of the safety shield. The configuration of the trigger will depend on the bias force on the operating member and the amount of movement required of the locking member to release the retraction member. The use of one piece, metal or plastic strips or leaf springs to form the locking and releasing mechanisms facilitates assembly while assembly of multi-part locking and releasing mechanisms can be facilitated by use of a case to produce a module for installation in a hub.

The distance that the distal end of the safety shield protrudes beyond the distal end of the trocar upon penetration can be selected in accordance with the surgical procedure to be performed and the cavity to be penetrated with the distance being selected to correspond to a potential space to be created within the body cavity upon introduction of the portal sleeve therein. The distal end of the safety shield can be formed with various configurations to safely contact and move an adjacent tissue layer away from the cavity wall upon penetration therein with the automatic retractable safety trocar instrument. With the safety shields in the extended position upon penetration of the retractable safety penetrating trocar instruments into body cavities and the trocars retracted within the instruments, redundant protection and safety is provided to avoid damage to tissue and organ structures within the cavity.

Insofar as the present invention is subject to many variations, modifications and changes in detail, it is intended that all subject matter discussed above or shown in the accompanying drawings be interpreted as illustrative only and not be taken in a limiting sense.

What is claimed is:

1. A method of forming a space between a wall of an anatomical cavity and a layer of tissue within the cavity comprising the steps of
   penetrating the cavity wall with a sharp tip of a penetrating member disposed within a portal sleeve to position a distal end of the portal sleeve within the cavity;
   automatically extending a safety shield to an extended position with a distal end of the safety shield protecting the sharp tip of the penetrating member and protruding beyond the distal end of the portal sleeve a distance corresponding to a size of a potential space to be formed between the tissue and the cavity wall; and
   contacting the tissue with the distal end of the safety shield to move the tissue away from the cavity wall to form a space having a size between the tissue and the cavity wall corresponding to the distance.

2. A method of forming a space as recited in claim 1 wherein the safety shield is disposed between the portal sleeve and the penetrating member and is biased to the extended position and further including, prior to said step of penetrating, moving the safety shield to a retracted position against the bias to expose the sharp tip of the penetrating member.

3. A method of forming a space as recited in claim 2 wherein said step of moving includes aligning the distal end of the safety shield with the penetrating member and the portal sleeve to create a substantially smooth profile with the penetrating member and the distal end of the portal sleeve.

4. A method of forming a space as recited in claim 1 further including controlling the amount of extension of the safety shield in accordance with the size of the potential space to be created.

5. A method of maintaining a space between a wall of an anatomical cavity and a layer of tissue within the cavity comprising the steps of
   penetrating the cavity wall with a sharp tip of a penetrating member disposed within a portal sleeve to position a distal end of the portal sleeve within the cavity;
   automatically extending a safety shield to protrude beyond the sharp tip of the penetrating member and the cavity wall upon positioning of the portal sleeve distal end within the cavity; and
   contacting the layer of tissue with the blunt end of the safety shield and moving the tissue away from the wall with the blunt end of the safety shield in response to automatic extension of the safety shield to maintain a space between the tissue and the wall.

6. A method of maintaining a space as recited in claim 5 and further including biasing the safety shield to normally protrude beyond the sharp tip of the penetrating member and, prior to the step of penetrating, moving the safety shield against the bias to expose the sharp tip of the penetrating member.

7. A method of maintaining a space as recited in claim 6 wherein said step of moving includes forcing the safety shield against the cavity wall to overcome the bias with a force from the cavity wall.

8. A method of maintaining a space as recited in claim 7 wherein said step of moving includes limiting movement of the safety shield against the bias.

9. A method of maintaining a space as recited in claim 7 wherein said step of automatically extending includes moving the safety shield toward the normally protruding position with the bias upon removal of the force from the cavity wall.

10. A method of maintaining a space as recited in claim 9 wherein the safety shield is disposed between the portal sleeve and the penetrating member and further including, after said step of automatically extending, completely withdrawing the penetrating member and the safety shield from the portal sleeve leaving the distal end of the portal sleeve within the anatomical cavity.

11. A retractable safety penetrating instrument for penetration into an anatomical cavity comprising
 a portal sleeve having a distal end and a proximal end;
 a penetrating member slidably disposed in said portal sleeve and having a sharp distal end for penetrating tissue;
 a safety shield disposed between said portal sleeve and said penetrating member and having a distal end;
 retracting means for automatically moving said sharp distal end from an operative position wherein said sharp distal end protrudes beyond said portal sleeve distal end to a retracted, protected position wherein said sharp distal end is disposed proximally of said operative position in response to penetration of said portal sleeve distal end into an anatomical cavity; and
 extending means for automatically extending said safety shield to an extended position wherein said safety shield distal end protrudes beyond said portal sleeve distal end in response to penetration of said portal sleeve distal end into the anatomical cavity.

12. A retractable safety penetrating instrument as recited in claim 11 further including means for releasably locking said penetrating member in said retracted position and allowing said penetrating member to be manually moved to said operative position.

13. A retractable safety penetrating instrument as recited in claim 12 wherein said penetrating member includes a proximal end and further including a hub mounting said proximal end of said penetrating member and said means for releasably locking includes a pin on said penetrating member and a slot in said hub for receiving said pin, said slot having a longitudinal slot portion with a proximal end at which said pin is disposed with the penetrating member in the retracted position and a proximal transverse slot portion into which the pin is movable to lock said penetrating member in the retracted position, said pin being movable from the proximal transverse slot portion distally along the longitudinal slot portion to move said penetrating member to the operative position.

14. A retractable safety penetrating instrument as recited in claim 13 further including means for locking said penetrating member in the operative position.

15. A retractable safety penetrating instrument as recited in claim 14 wherein said means for locking includes a distal transverse slot portion of said slot into which the pin can be moved with the penetrating member in the operative position to prevent movement of the penetrating member to the retracted position.

16. A retractable safety penetrating instrument as recited in claim 11 wherein said means for extending includes means for biasing said safety shield distally.

17. A retractable safety penetrating instrument as recited in claim 16 wherein said safety shield includes a proximal end and further including a hub mounting said proximal end of said safety shield and a flange at said proximal end of said safety shield disposed in said hub and wherein said biasing means includes a spring connected between said flange and said hub.

18. A retractable safety penetrating instrument as recited in claim 17 wherein said retracting means includes means for biasing said penetrating member in a proximal direction.

19. A retractable safety penetrating instrument as recited in claim 18 wherein said penetrating member includes a proximal end and further including a tube secured to said hub and extending into said proximal end of said penetrating member and said means for biasing said penetrating member includes a spring mounted within said penetrating member between said tube and said hub.

20. A retractable safety penetrating instrument as recited in claim 19 wherein said safety shield biasing means is normally in a relaxed, unloaded state with said safety shield in the extended position.

21. A retractable safety penetrating instrument as recited in claim 20 wherein said instrument is supplied with said penetrating member in the retracted position and said means for biasing said penetrating member is in a relaxed, unloaded state in the retracted position for the penetrating member.

22. A retractable safety penetrating instrument as recited in claim 11 wherein said penetrating member and said safety shield include proximal ends and further including a hub mounting said proximal ends of said penetrating member and said safety shield and a housing mounting said proximal end of said portal sleeve with said safety shield extending through a passage in said housing and wherein said safety shield and penetrating member are removable from said portal sleeve.

23. A retractable safety penetrating instrument as recited in claim 22 further including a valve assembly mounted in said housing to create a seal with said passage upon removal of said safety shield and penetrating member from said portal sleeve.

24. A retractable safety penetrating instrument as recited in claim 23 wherein said valve assembly includes a one-piece, integral valve mounted in said passage.

25. A retractable safety penetrating instrument as recited in claim 22 further including an insert removably mounted in said hub and coupled with said proximal end of said penetrating member allowing said penetrating member to be withdrawn from said safety shield leaving said safety shield in place within said portal sleeve.

26. A retractable safety penetrating instrument as recited in claim 25 further including a tube extending from said insert into said proximal end of said penetrating member and wherein said proximal end of said penetrating member is formed of a first color, said tube is formed of a second color and a portion of said hub overlying tube is transparent with the color of the tube being visible through the transparent portion when the penetrating member is in the operative position and the color of the proximal end of the penetrating member being visible through the transparent portion when the penetrating member is in the retracted position.

27. A retractable safety penetrating instrument for forming a portal communicating with a cavity in the body to allow passage of instruments for penetrating least invasive medical procedures comprising
 a portal sleeve for providing a passage through a cavity wall and having a distal end for positioning in the body cavity, a proximal end for positioning externally of the body cavity and a lumen extending between said distal and proximal ends;

a penetrating member disposed in said lumen of said portal sleeve and having a sharp distal end for penetrating the cavity wall;

retracting means for moving said penetrating member proximally relative to said portal sleeve from an operative position wherein said sharp distal end protrudes beyond said portal sleeve distal end to a retracted position to prevent contact of said sharp distal end with tissue;

a safety shield disposed between said portal sleeve and said penetrating member and having a distal end normally protruding distally beyond the distal end of the portal sleeve, said safety shield being movable proximally from the normally protruding position during penetration of the cavity wall and movable distally thereafter toward the normally protruding position; and trigger means for automatically actuating said retracting means to move said penetrating member to the retracted position in response to distal movement of said safety shield, relative to said portal sleeve, upon said portal sleeve distal end entering the body cavity.

28. A retractable safety penetrating instrument as recited in claim 27 wherein said trigger means includes means for controlling the distance that said safety shield distal end protrudes beyond said distal end of said portal sleeve prior to retraction of said penetrating member.

29. A retractable safety penetrating instrument as recited in claim 27 wherein said retracting means includes means for moving said safety shield to a retracted position within said portal sleeve simultaneously with retraction of said penetrating member.

30. A method of maintaining a space between a wall of an anatomical cavity and a layer of tissue within the cavity comprising the steps of biasing a safety shield to normally protrude beyond a sharp tip of a penetrating member disposed within a portal sleeve;

moving the safety shield against the bias to expose the sharp tip of the penetrating member, said step of moving including forcing the safety shield against the cavity wall to overcome the bias with a force from the cavity wall and limiting movement of the safety shield against the bias, said step of limiting including preventing further movement of the safety shield against the bias upon alignment of the safety shield with a distal end of the portal sleeve;

penetrating the cavity wall with the sharp tip of the penetrating member to position the distal end of the portal sleeve within the cavity; and automatically extending the safety shield to protrude beyond the sharp tip of the penetrating member and the cavity wall upon positioning of the portal sleeve distal end within the cavity whereby a blunt distal end of the safety shield contacts the layer of tissue and moves the tissue away from the wall maintaining a space between the tissue and the wall.

31. A method of maintaining a space between a wall of an anatomical cavity and a layer of tissue within the cavity comprising the steps of biasing a safety shield to normally protrude beyond a sharp tip of a penetrating member disposed within a portal sleeve;

moving the safety shield against the bias to expose the sharp tip of the penetrating member, said step of moving including forcing the safety shield against the cavity wall to overcome the bias with a force from the cavity wall and limiting movement of the safety shield against the bias, said step of limiting including preventing further movement of the safety shield against the bias upon alignment of the safety shield with a distal end of the penetrating member;

penetrating the cavity wall with the sharp tip of the penetrating member to position a distal end of the portal sleeve within the cavity; and automatically extending the safety shield to protrude beyond the sharp tip of the penetrating member and the cavity wall upon positioning of the portal sleeve distal end within the cavity whereby a blunt distal end of the safety shield contacts the layer of tissue and moves the tissue away from the wall maintaining a space between the tissue and the wall.

32. A method of maintaining a space between a wall of an anatomical cavity and a layer of tissue within the cavity comprising the steps of biasing a safety shield disposed within a portal sleeve to normally protrude beyond a sharp tip of a penetrating member received in a lumen of the safety shield;

moving the safety shield against the bias to expose the sharp tip of the penetrating member, said step of moving including forcing the safety shield against the cavity wall to overcome the bias with a force from the cavity wall;

penetrating the cavity wall with the sharp tip of the penetrating member to position a distal end of the portal sleeve within the cavity;

automatically extending the safety shield to protrude beyond the sharp tip of the penetrating member and the cavity wall upon positioning of the portal sleeve distal end within the cavity whereby a blunt distal end of the safety shield contacts the layer of tissue and moves the tissue away from the wall maintaining a space between the tissue and the wall, said step of automatically extending includes moving the safety shield toward the normally protruding position with the bias upon removal of the force from the cavity wall; and completely withdrawing the penetrating member from the lumen of the safety shield leaving the distal end of the safety shield within the anatomical cavity.

33. A method of maintaining a space as recited in claim 32 and further including, after said step of withdrawing, performing a medical procedure within the anatomical cavity through the lumen of the safety shield.

34. A method of maintaining a space as recited in claim 33 wherein the distal end of the safety shield has at least one aperture and said step of performing includes introducing fluid in the anatomical cavity through the aperture.

35. A method of maintaining a space as recited in claim 33 wherein the distal end of the safety shield has at least one aperture and said step of performing includes aspirating fluid from the anatomical cavity through the aperture.

36. A method of maintaining a space between a wall of an anatomical cavity and a layer of tissue within the cavity comprising the steps of penetrating the cavity wall with a sharp tip of a penetrating member disposed within a portal sleeve to position a distal end of the portal sleeve within the cavity;

automatically retracting the penetrating member to a safety protected position wherein the sharp tip is not exposed within the anatomical cavity upon positioning of the portal sleeve distal end within the cavity; and automatically extending a safety shield to protrude beyond the sharp tip of the penetrating member and the cavity wall upon positioning of the portal sleeve distal end within the cavity whereby a blunt distal end of the safety shield contacts the layer of tissue and moves the tissue away from the wall maintaining a space between the tissue and the wall.

37. A method of maintaining a space as recited in claim 36 wherein said step of automatically retracting includes retracting the sharp tip of the penetrating member within the portal sleeve.

38. A method of maintaining a space as recited in claim 37 wherein said step of automatically retracting includes retracting the penetrating member in response to movement of the safety shield toward the normally protruding position.

39. A method of forming a space between a wall of an anatomical cavity and a layer of tissue within the cavity comprising the steps of biasing a safety shield disposed between a portal sleeve and a penetrating member to an extended position wherein a distal end of the safety shield protects a sharp tip of the penetrating member and protrudes beyond a distal end of the portal sleeve a distance corresponding to a size of a potential space to be formed between the tissue and the cavity wall;

moving the safety shield to a retracted position against the bias to expose the sharp tip of the penetrating member, said step of moving including aligning the distal end of the safety shield with the penetrating member and the portal sleeve to create a substantially smooth profile with the penetrating member and the distal end of the portal sleeve, and wherein the penetrating member includes a trocar having a conical distal end proximally joined to a cylindrical neck at a junction and a conical shoulder proximally joining the neck to a trocar body and the safety shield includes a conical distal end having an angular inner surface segment and a cylindrical inner surface segment extending distally from the angular inner surface segment to a distal peripheral edge, said step of aligning including positioning the angular inner surface segment to extend along the conical trocar shoulder, the cylindrical inner surface segment to extend along the trocar neck and the distal peripheral edge at the junction;

penetrating the cavity wall with the sharp tip of the penetrating member to position the distal end of the portal sleeve within the cavity;

automatically extending the safety shield to the extended position; and contacting the tissue with the distal end of the safety shield to move the tissue away from the cavity wall to form a space having a size between the tissue and the cavity wall corresponding to the distance.

40. A method of forming a space between a wall of an anatomical cavity and a layer of tissue within the cavity comprising the steps of biasing a safety shield disposed between a portal sleeve and a penetrating member to an extended position with a distal end of the safety shield protecting a sharp tip of the penetrating member and protruding beyond a distal end of the portal sleeve a distance corresponding to a size of a potential space to be formed between the tissue and the cavity wall;

moving the safety shield to a retracted position against the bias to expose the sharp tip of the penetrating member, the penetrating member being movable between a retracted position with the sharp tip disposed within the portal sleeve and an operative position with the sharp tip disposed beyond the distal end of the portal sleeve;

setting the penetrating member in the operative position;

penetrating the cavity wall with the sharp tip of the penetrating member to position the distal end of the portal sleeve within the cavity;

automatically extending the safety shield to the extended position; and contacting the tissue with the distal end of the safety shield to move the tissue away from the cavity wall to form a space having a size between the tissue and the cavity wall corresponding to the distance.

41. A method of forming a space as recited in claim 40 wherein the penetrating member is normally biased to the retracted position and said step of setting includes moving the penetrating member to the operative position against the bias and locking the penetrating member in the operative position.

42. A method of forming a space as recited in claim 41 wherein the penetrating member includes a proximal end mounted in a hub and a pin projecting from the penetrating member through a slot in the hub having a longitudinal slot portion, a distal transverse slot portion and a proximal transverse slot portion with the pin being disposed at a proximal end of the longitudinal slot portion in the retracted position for the penetrating member, and said step of setting and locking includes manually moving the pin distally along the longitudinal slot portion and rotating the pin into the distal transverse slot portion with the penetrating member in the operative position to prevent movement of the penetrating member to the retracted position.

43. A method of forming a space as recited in claim 41 wherein the penetrating member includes a proximal end mounted in a hub having a latch and a pin projecting from the penetrating member proximal end through a slot in the hub having a longitudinal slot portion, a distal transverse slot portion and a proximal transverse slot portion with the pin being disposed at a proximal end of the longitudinal slot portion in the retracted position for the penetrating member, and said step of setting and locking incudes manually moving the pin distally along the longitudinal slot portion and automatically engaging the proximal end of the penetrating member with the latch when the penetrating member is in the operative position to prevent movement of the penetrating member to the retracted position.

44. A method of forming a space as recited in claim 43 and further including confirming locking of the penetrating member in the operative position by feel.

45. A method of forming a space as recited in claim 43 and further including aurally confirming locking of the penetrating member in the operative position.

46. A method of forming a space as recited in claim 43 and further including visually confirming locking of the penetrating member in the operative position.

47. A method of forming a space as recited in claim 46 wherein said step of visually confirming includes observing a color change through the hub.

48. A method of forming a space as recited in claim 47 wherein the penetrating member proximal end is made a first predetermined color and further including a tube made a second predetermined color and secured to the hub to extend into the proximal end of the penetrating member with a portion of the hub overlying the tube being transparent and said step of visually confirming includes observing the color of the tube through the hub when the penetrating member is in the operative position.

49. A method of forming a space as recited in claim 43 and further including automatically retracting the penetrating member to the retracted position upon positioning of the portal sleeve distal end in the cavity.

50. A method of forming a space as recited in claim 49 wherein said step of automatically retracting includes automatically releasing the penetrating member from the latch allowing the penetrating member to return automatically to the retracted position upon introduction of the distal end of the portal sleeve into the cavity.

51. A method of forming a space as recited in claim 50 wherein said step of automatically retracting includes, after said contacting step, automatically retracting the safety shield within the portal sleeve.

52. A method of forming a space as recited in claim 50 further including confirming retraction of the penetrating member by feel.

53. A method of forming a space as recited in claim 50 further including aurally confirming retraction of the penetrating member.

54. A method of forming a space as recited in claim 50 further including visually confirming retraction of the penetrating member.

55. A method of forming a space as recited in claim 54 wherein said step of visually confirming includes observing a color change.

56. A method of forming a space as recited in claim 55 wherein the penetrating member proximal end is made a first predetermined color and further including a tube made a second predetermined color and further including a tube secured to the hub to extend into the proximal end of the penetrating member with a portion of the hub overlying the tube being transparent and said step of visually confirming includes observing the color of the penetrating member proximal end through the hub when the penetrating member is in the retracted position.

57. A method of forming a space as recited in claim 50 wherein said step of automatically retracting includes retracting the penetrating member in response to extending the safety shield.

58. A method of forming a space as recited in claim 57 and further including controlling the distance that the distal end of the safety shield protrudes beyond the distal end of the portal sleeve prior to retraction of the penetrating member.

59. A method of forming a space as recited in claim 43 further including, prior to said setting and locking step, locking the penetrating member in the retracted position.

60. A method of forming a space as recited in claim 59 wherein said step of locking the penetrating member in the retracted position includes rotating the pin into the proximal transverse slot portion.

* * * * *